United States Patent [19]

Hellmuth et al.

[11] Patent Number: 5,537,162
[45] Date of Patent: Jul. 16, 1996

[54] METHOD AND APPARATUS FOR OPTICAL COHERENCE TOMOGRAPHIC FUNDUS IMAGING WITHOUT VIGNETTING

[75] Inventors: Thomas Hellmuth, Danville; Jay Wei, Fremont, both of Calif.

[73] Assignee: Carl Zeiss, Inc., Thornwood, N.Y.

[21] Appl. No.: 169,705

[22] Filed: Dec. 17, 1993

[51] Int. Cl.$^6$ .................................................. A61B 3/14
[52] U.S. Cl. ..................... 351/206; 351/211; 351/221
[58] Field of Search ............................ 351/206, 211, 351/212, 221; 354/62

[56] References Cited

U.S. PATENT DOCUMENTS

| | | | |
|---|---|---|---|
| 4,406,542 | 9/1983 | Boggy et al. | 356/345 |
| 4,900,144 | 2/1990 | Kobayashi | 351/206 |

FOREIGN PATENT DOCUMENTS

| | | | |
|---|---|---|---|
| 3926652 | 4/1991 | Germany | 351/221 |

OTHER PUBLICATIONS

"Feurtosecond Optical Ranging in Biological Systems" by J. G. Fujimoto et al. Optics Letters, vol. 10, No. 3, Mar. 1986, pp. 150–152.

"New Measurement System for Fault Location in Optical Waveguide Devices Based on Interferometric Technique" by K. Takada et al. Applied Optics, vol. 26, No. 9, May 1, 1987, pp. 1603–1606.

Section 7.5.8 of "Principles of Optics" 6th Edition, M. Born and E. Wolf, Pergamon Press, New York (1986) (No Month).

"Optical Coherence Tomography" by Huang et al., Science, 254, Nov., 22, 1991, pp. 1178–1181.

Ph.D. thesis "Optical Coherence Tomography" David Huang, Massachusetts Institute of Technology, May, 1993.

*Primary Examiner*—William L. Sikes
*Assistant Examiner*—James A. Dudek
*Attorney, Agent, or Firm*—Michael B. Einschlag

[57] ABSTRACT

Apparatus for illuminating the fundus of an eye with a scanned sample beam of radiation, the scanned sample beam emerging from a beam scanner which is exposed to a sample beam, which apparatus is for use in optical coherence tomography. An embodiment of the apparatus includes: (a) scanner lens and a beamsplitter for transferring radiation from the scanned sample beam, including chief rays of the sample beam which emerge from a point of final deflection of the beam scanner, and (b) a lens for focusing the transferred radiation so that the scanned sample beam is focused onto the fundus by the eye. In accordance with the invention the scanner lens is fixed with respect to the beam scanner so that the point of final deflection is located substantially in the back focal plane of the scanner lens and the scanner lens is movable.

17 Claims, 5 Drawing Sheets

Side View of Retroreflecting Prism 404

METHOD AND APPARATUS FOR OPTICAL COHERENCE TOMOGRAPHIC FUNDUS IMAGING WITHOUT VIGNETTING

TECHNICAL FIELD OF THE INVENTION

The present invention relates to method and apparatus for optical coherence tomographic ("OCT") fundus imaging.

BACKGROUND OF THE INVENTION

At present, two techniques of reflectometry are undergoing intensive research and development efforts, the two techniques being optical time domain reflectometry ("OTDR") and optical coherence domain reflectometry ("OCDR"). OTDR is an optical analog of radar and sonar. In accordance with OTDR, short light pulses having pulse durations in picoseconds, or even femtoseconds, are emitted from a suitable laser source and impinge upon a sample. The light pulses are reflected from various structures comprising the sample and the reflected pulses are detected by a time resolving detector. The distance between each reflecting surface of the sample and the detector is determined by reason of its proportionality to the time of flight of the light pulses from the light source to the reflecting surface and back again. In practice, the detection system can be a nonlinear, optical, cross correlation apparatus such as that described in an article entitled "Femtosecond Optical Ranging in Biological Systems" by J. G. Fujimoto et al., published in *Optics Letters*, Vol. 10, No. 3, March 1986, pp. 150–152. As described in the article, a beam of light reflected from the sample is superimposed upon a light pulse train emitted by the source in a nonlinear optical crystal. The optical pathlength of the reference beam is varied by moving a reference mirror which is mounted on a translation stage.

The resolution of the OTDR technique can be further improved by an optical coherence domain reflectometry ("OCDR") technique which is described, for example, in an article entitled "New Measurement System for Fault Location in Optical Waveguide Devices Based on an Interferometric Technique" by K. Takada et al., published in *Applied Optics*, Vol. 26, No. 9, May 1, 1987, pp. 1603–1606. In accordance with OCDR, a broad band, continuous wave source is used (in accordance with OTDR a pulsed light source is used). As shown in Section 7.5.8 of a book entitled "Principles of Optics," 6th Edition, M. Born and E. Wolf, Pergamon Press, New York (1986), the coherence length L of the broad band, continuous wave light source is related to its bandwidth B by the following equation:

$$L = c/B$$

where c is the velocity of light. In accordance with OCDR, output from the source is separated into two beams by a beamsplitter. One of the beams impinges upon a mirror which is referred to below as a reference mirror. The other one of the beams is directed to impinge upon a sample. Light reflected from the sample is superimposed with light reflected from the reference mirror. The superimposed beams interfere if the optical path difference between the two beams is smaller than the coherence length of the light source. Further, in accordance with OCDR, the reference mirror is moved with a constant velocity. As a result, the interference is detected as a periodic variation of a detector signal having a frequency equal to a Doppler shift frequency which is introduced by moving the reference mirror with the constant velocity. The interference signal vanishes as soon as the optical path difference between the beam reflected from the sample and the beam reflected from the reference mirror becomes larger than the coherence length of the light source. As those skilled in the art readily appreciate, displacement of the reference mirror must be in a range which corresponds to the depth of the sample to be imaged. Hence, OCDR is a technique which provides optical ranging with a high resolution, which resolution is limited only by the bandwidth of the light source.

OCDR is combined with a transverse scanning device to acquire three-dimensional images of semi-transparent objects such as the retina of the human eye in a technique which is referred to in the art as optical coherence tomography ("OCT"). This technique has been described, for example, in an article entitled "Optical Coherence Tomography" by Huang et al., published in *Science*, 254, Nov. 22, 1991, pp. 1178–1181.

In ophthalmoscopic applications of OCT, it is necessary to locate the field of interest on the fundus, i.e., the location where the retina is to be scanned by an OCT sample beam. FIG. 1 shows a figure from a Ph.D. thesis entitled "Optical Coherence Tomography" by David Huang, Massachusetts Institute of Technology, May, 1993 wherein a sample arm fiber of an OCT system is coupled to slitlamp biomicroscope 2000, a clinical instrument commonly used for examination of the eye. As shown in FIG. 1, a transverse scanning mechanism is mounted on slitlamp biomicroscope 2000 and two galvanometer driven motors allow the sample beam to be scanned in an arbitrary pattern on the retina. FIG. 1 shows OCT imaging device 2000 consisting of slitlamp viewing optics 2010 and ocular lens 2020 to image the fundus. As shown in FIG. 1, sample beam 2050, output from sample arm fiber 2060, is collimated by collimating lens 2070 and steered by orthogonally mounted, galvanometer driven mirrors 2030 and 2040. Focusing lens 2080 and dichroic mirror 2090 direct the sample beam into the image plane of slitlamp biomicroscope 2000. Then, ocular lens 2020, in combination with the optics of eye 2100, relays the image plane of slitlamp biomicroscope 2000 onto the retina. As disclosed, focusing lens 2080 and ocular lens 2020 form a telecentric system so that the sample beam which impinges upon galvanoscanner 2030 is imaged into the entrance pupil of eye 2100 and, as a result, vignetting is minimized. In addition, a red pilot beam is arranged to travel colinearly with the sample beam to enable an operator to see where the infrared sample beam is located on the fundus.

The ophthalmoscopic application of OCT shown in FIG. 1, and described in the thesis, suffers from several disadvantages. The first disadvantage results from the fact that the refractive error of a human eye varies within a range of up to ±20 diopters. Therefore, there is a need to focus the sample beam and the imaging optics of slitlamp biomicroscope 2000 to compensate for the refractive error of the human eye. However, in the apparatus shown in FIG. 1, focusing lens 2080 and slitlamp viewing optics 2010 are fixed. As a result, the required focusing is accomplished by moving ocular lens 2020 along the optical axis of slitlamp biomicroscope 2000. A disadvantage of this is that the image of galvanometer driven mirror 2030, as well as the image of slit illumination 2110, moves relative to the pupil of eye 2100 when ocular lens 2020 is adjusted. Thus, one must refocus illumination 2110 by moving microscope 2000. Then, one must refocus the image of the fundus, and so forth, to iterate to a position wherein both illumination 2110 and mirror 2030 are properly focused.

The second disadvantage results from adjustments which are typically made to overcome the effect of using a bright illumination light source in fundus imaging. It is necessary to use a bright illumination light source in fundus imaging because the low backscattering efficiency of the fundus (the fundus reflectivity is approximately 10-4) would otherwise result in a fundus image having a rather low light level. As shown in FIG. 1, and as described in the thesis, slit illumination 2110 is imaged into the eye pupil by ocular lens 2020. The reflectivity of the cornea of the eye and the reflectivity of ocular lens 2020 (in practice ocular lens 2020 is a Volk double aspheric bio lens manufactured by Volk of 7893 Enterprise Drive, Mentor, Ohio 44060) are both on the order of 4%, which reflectivities are much greater than that of the fundus. Therefore, it is necessary to make adjustments to keep backreflections from the cornea and from ocular lens 2020 out of the observation path of slit biomicroscope 2000. As disclosed in an instruction manual entitled "VOLK Double Aspheric Bio Lenses" published by Volk of Mentor, Ohio, at p. 3, adjustments are made to reduce backreflections by tilting slit illumination 2110 relative to the optical axis and by tilting ocular lens 2020. However, these adjustments cause astigmatism and vignetting.

In light of the above, there is a need in the art for method and apparatus for OCT fundus imaging which overcomes the above-described problems.

SUMMARY OF THE INVENTION

Advantageously, embodiments of the present invention overcome the above-described problems in the art and provide method and apparatus for OCT fundus imaging.

A first aspect of the present invention is apparatus for illuminating the fundus of an eye with a scanned sample beam of radiation, the scanned sample beam emerging from a beam scanner which is exposed to a sample beam, which apparatus is for use in optical coherence tomography and which apparatus comprises: (a) means for transferring radiation from the scanned sample beam, including chief rays of the sample beam which emerge from a point of final deflection of the beam scanner, and (b) means for focusing the transferred radiation so that the scanned sample beam is focused onto the fundus by the eye. The means for transferring comprises a lens means which is fixed with respect to the beam scanner so that the point of final deflection is located substantially in the back focal plane of the lens means and the lens means is movable. In one particular embodiment of this aspect of the present invention, the means for focusing comprises an ocular lens of a fundus camera and the means for transferring further comprises a beamsplitter disposed to direct output from the lens means to the ocular lens.

A second aspect of the present invention is apparatus for illuminating the fundus of an eye with a scanned sample beam of radiation, the scanned sample beam emerging from a beam scanner which is exposed to a sample beam, which apparatus is for use in optical coherence tomography and which apparatus comprises: (a) means for transferring radiation from the sample beam, including chief rays of the sample beam which emerge from a point of final deflection of the beam scanner, and (b) means for focusing the transferred radiation so that the scanned sample beam is focused onto the fundus by the eye. The means for transferring is fixed with respect to the beam scanner and at least a first portion of the focusing means so that the point of final deflection is located substantially in the back focal plane of the first portion of the focusing means and the first portion of the focusing means is movable. In one particular embodiment of this aspect of the present invention, the at least a first portion of the focusing means comprises an internal focusing lens of a fundus camera and the means for transferring comprises a beamsplitter disposed to direct the scanned sample beam to impinge upon the internal focusing lens.

BRIEF DESCRIPTION OF THE FIGURE

Components which are the same in the various figures have been designated by the same numerals for ease of understanding.

DETAILED DESCRIPTION

Figure 1:
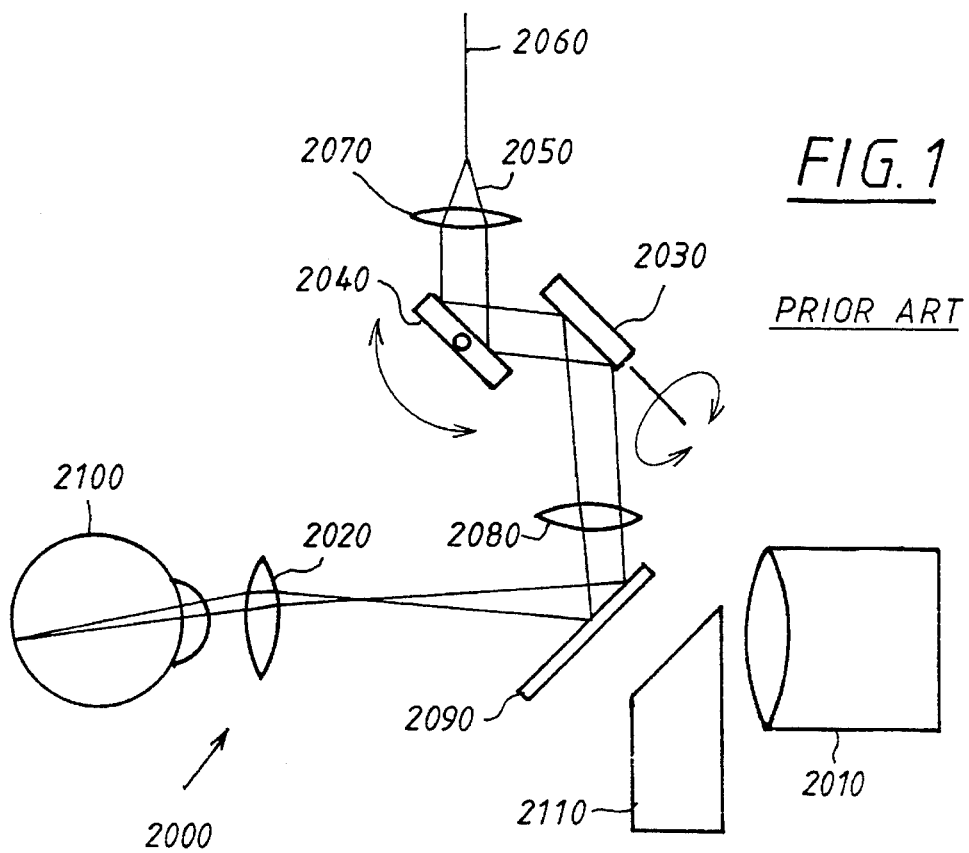
FIG. 1 shows, in pictorial form, a prior art OCT apparatus which utilizes a slitlamp biomicroscope.
Figure 2:
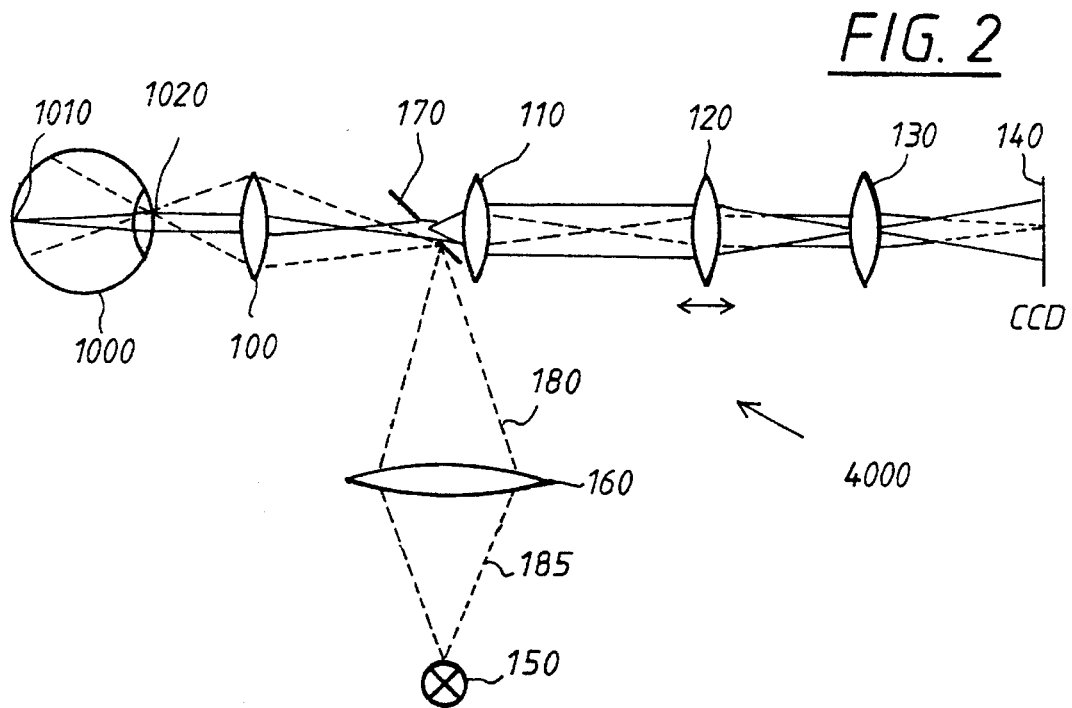
FIG. 2 shows, in pictorial form, a fundus camera.

FIG. 2 shows, in pictorial form, a typical fundus camera 4000. As shown in FIG. 2, ocular lens 100 generates an intermediate image of fundus 1010 of a patient's eye 1000. In the case of an emetropic eye, the intermediate fundus image generated by ocular lens 100 is located in the back focal plane of ocular lens 100. Relay lens 110 is a transfer lens which generates a further intermediate image of fundus 1010. Finally, the intermediate fundus image generated by relay lens 110 is imaged to CCD target 140 of a video port of fundus camera 4000 by internal focusing lens 120 and tube lens 130. Illumination of fundus 1010 is provided by light source 150. Output beam 185 from light source 150 is focused as beam 180 onto geometrical beamsplitter 170 which is placed behind ocular lens 100 at an image of eye pupil 1020 of eye 1000. As is well known to those skilled in the art, a geometrical beamsplitter is a mirror, with an aperture, for reflecting a portion of a beam and for transmitting a portion of a beam and, as shown in FIG. 2, geometrical beamsplitter 170 reflects illumination beam 180 and transmits the observation beam. As shown in FIG. 2, output beam 185 from source 150 is focused onto geometrical beamsplitter 170 in such a manner that ocular lens 100 focuses the reflection of beam 180 on eye pupil 1020 of eye 1000 in an "off-center" configuration. Hence, the path of output beam 185 from source 150 and the path of the observation beam which reaches CCD 140 are separated in the anterior chamber of eye 1000. As a result, almost no light from output beam 185 is scattered back into the observation path of fundus camera 4000.

As shown in FIG. 2, and as occurs in a typical fundus camera, ocular lens 100, relay lens 110, and tube lens 130 are fixed and internal focusing lens 120 is movable. In practice, fundus camera 4000 is physically moved into position so that output beam 185 from light source 150 is focused on eye pupil 1020. Then, internal focusing lens 120 is used to focus fundus 1010 on CCD 140. As shown in FIG. 2, geometrical beamsplitter 170 constitutes the aperture stop of the observation path and it is located at the focal plane of relay lens 110 so that the aperture is imaged to infinity (telecentricity). Finally, internal focusing lens 120 images pupil 1020 into tube lens 130, and tube lens 130 ensures that the magnification of the whole system does not change when internal focusing lens 120 is moved to focus the image of fundus 1010 on CCD 140.

Further beamsplitters are typically positioned between tube lens 130 and internal focusing lens 120 for use as an additional observational port.

Figure 3:
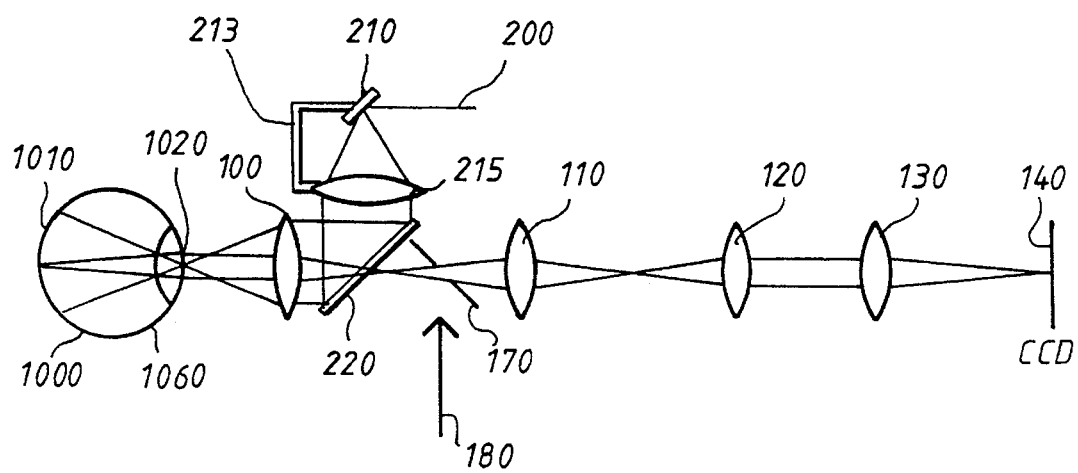
FIG. 3 shows, in pictorial form, an embodiment of the present invention for use in connection with the fundus camera shown in FIG. 2.

FIG. 3 shows, in pictorial form, an embodiment of the present invention for use in connection with fundus camera 4000 shown in FIG. 2. Since ocular lens 100 is fixed, it is necessary to focus sample beam 200 separately. As shown in FIG. 3, sample beam 200 impinges upon beam scanner 210. Beam scanner 210 may be fabricated, for example, as a galvanometric beam scanner such as the one that is disclosed in the thesis discussed in the Background of the Invention. The hatched lines in FIG. 3 show the manner in which beam scanner 210 moves sample beam 200 and the manner in which sample beam 200 is imaged into eye pupil 1020. The chief rays of sample beam 200, at various scan positions of beam scanner 210, describe a ray pencil which emerges from the center of beam scanner 210. In general, the chief rays describe a ray pencil which emerges from a point of final deflection of beam scanner 210 since beam scanner 210 may be comprised of several deflectors and/or mirrors. In accordance with the present invention: (a) the point of final deflection of beam scanner 210 is disposed substantially in the back focal plane of scanner lens 215 which is mounted on movable stage 213 and (b) beam scanner 210 is rigidly connected to the movable stage of scanner lens 215 to ensure that the point of final deflection of beam scanner 210 is disposed substantially in the back focal plane of scanner lens 215 for substantially all focusing positions of scanner lens 215. As a result, the ray pencil is collimated by scanner lens 215. Then, the collimated light impinges upon beamsplitter 220 and beamsplitter 220 directs it to ocular lens 100. Ocular lens 100 is positioned so that collimated light impinging thereon is focused into eye pupil 1020. Finally, the sample beam is focused by the optics of eye 1000 onto fundus 1010. Thus, in accordance with the present invention, the point of final deflection of beam scanner 210 is imaged into eye pupil 1020 for all focusing positions because of the collimated space between ocular lens 100 and scanner lens 215. If this were not the case, then vignetting would occur whereby scanning of sample beam 200 would be limited by eye pupil 1020. As one can readily appreciate, in order to use the embodiment shown in FIG. 3, one must physically move fundus camera 4000 to focus illumination beam 180, adjust internal focusing lens 120 to focus the observation path, and adjust scanner lens 215 to focus the sample beam. Note that the point of final deflection of beam scanner 210 (which is imaged to the focal point of ocular lens 100 into eye pupil 1020) is not exactly focused into the same plane as the intermediate image of illumination source 150 which is located a finite distance from ocular lens 100 in the plane of geometrical beamsplitter 170. However, this is not critical because the distance between ocular lens 100 and geometrical beamsplitter 170 can be long compared to the focal length of ocular lens 100 so that the image of illumination source 150 is also almost in the same plane as the point of final deflection of beam scanner 210. Of course those skilled in the art readily appreciate that the term point of final deflection is not restricted to a single point but also encompasses an area in which the chief rays of the sample beam are finally deflected in the beam scanner.

Figure 4:
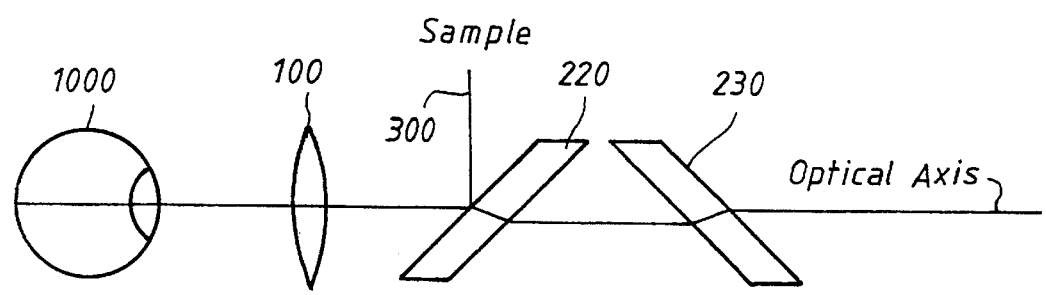
FIG. 4 shows, in pictorial form, a portion of the beamsplitter apparatus utilized in fabricating an embodiment of the present invention.

FIG. 4 shows, in pictorial form, a portion of the beamsplitter apparatus utilized in fabricating an embodiment of the present invention. Introduction of beamsplitter 220 into fundus camera 4000 causes a parallel shift of the optical axis of fundus camera 4000. In a fundus camera, the illumination optics is designed so that the vertex of ocular lens 100 is not illuminated. This is done to avoid reflections from ocular lens 100 back into the observation path. With the use of beamsplitter 220, the illumination cone is shifted and light beams may hit the vertex of ocular lens 100 and, thereby, cause false light to be reflected into the observation path. As shown in FIG. 4, this is avoided by the use of compensation plate 230. The thickness and tilt angle of compensation plate 230 are determined in accordance with methods which are well known to those skilled in the art to compensate for the shift of the optical axis introduced by beamsplitter 220. Also, compensation plate 230 eliminates coma caused by tilted beamsplitter plate 220.

Figure 5:
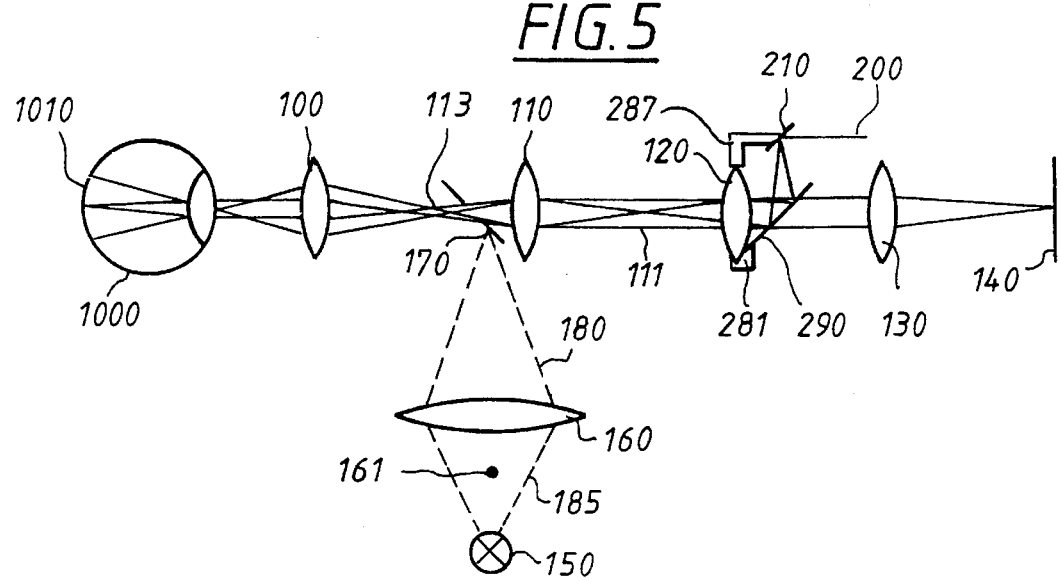
FIG. 5 shows, in pictorial form, a preferred embodiment of the present invention for use in connection with the fundus camera shown in FIG. 2.

FIG. 5 shows, in pictorial form, a preferred embodiment of the present invention for use in connection with fundus camera 4000 shown in FIG. 2. As shown in FIG. 5, OCT sample beam 200 is coupled into fundus camera 4000 behind internal focusing lens 120. As also shown in FIG. 5, sample beam 200 impinges upon beam scanner 210 which reflects sample beam 200 onto beamsplitter 290. Beamsplitter 290 reflects the sample beam to internal focusing lens 120. The chief rays of sample beam 200, at various scan positions of beam scanner 210, describe a ray pencil which emerges from the center of beam scanner 210. In general, the chief rays describe a ray pencil which emerges from a point of final deflection of beam scanner 210 since beam scanner 210 may be comprised of several deflectors and/or mirrors. In accordance with the present invention: (a) the point of final deflection of beam scanner 210 is disposed substantially in the back focal plane of internal focusing lens 120 and (b) mounting 281 for beamsplitter 290 and mounting 287 for beam scanner 210 are rigidly connected to internal focusing lens 120 so that they all move together. This ensures that the point of final deflection of beam scanner 210 is disposed substantially in the back focal plane of internal focusing lens 120 for substantially all focusing positions of internal focusing lens 120. As a result, the ray pencil is collimated by internal focusing lens 120 and is focused by relay lens 110 into the plane of geometrical beamsplitter 170. Then, ocular lens 100 focuses the ray pencil into eye pupil 1020. Thus, collimated sample beam 200 is focused by internal focusing lens 120 in intermediate image plane 111 which is conjugate with CCD target 140. Relay lens 110 images intermediate image plane 111 into intermediate image plane 113 which is equal to the back focal plane of ocular lens 100 in the case of an emetropic eye. Then, ocular lens 100 and the optics of eye 1000 focus the sample beam onto fundus 1010. Since mounting 281 for beamsplitter 290 and mounting 287 for beam scanner 210 are rigidly connected to internal focusing lens 120 so that they all move together, the point of final deflection of beam scanner 210 is always imaged into the plane of geometrical beamsplitter 170, independent of the position of internal focusing lens 120. Hence, the scanning sample beam is not vignetted by the aperture stop of geometrical beamsplitter 170. The preferred embodiment shown in FIG. 5 and described above is advantageous because: (a) the use of scanner lens 215 of FIG. 3 is avoided and (b) the sample beam and the observation path are focused together.

Figure 5A:
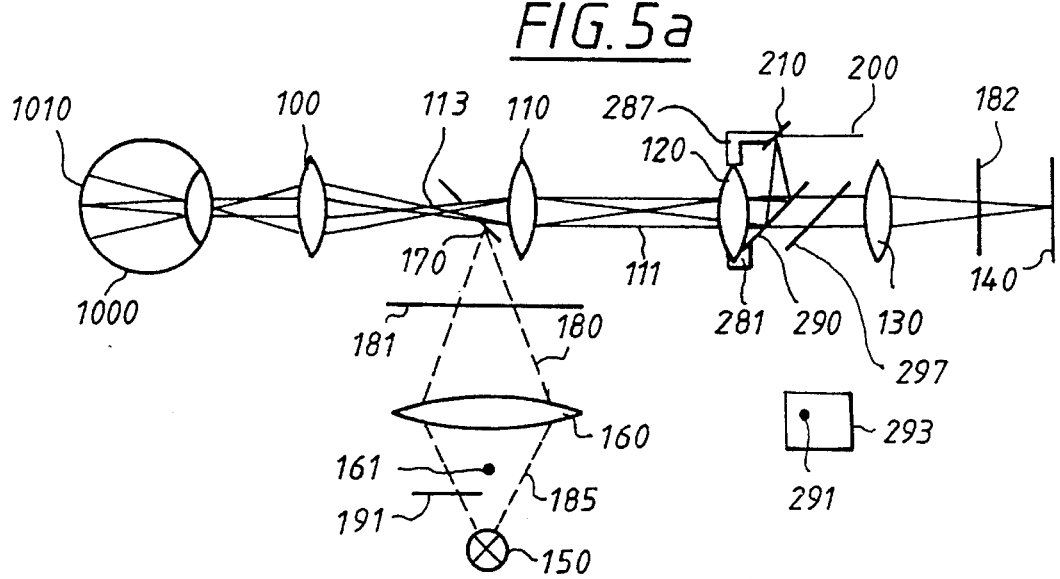
FIG. 5A shows, in pictorial form, the embodiment of FIG. 5 which further includes crossed polarizers and fixation targets.

FIG. 5A shows, in pictorial form, the embodiment of FIG. 5 which further includes crossed polarizers 181 and 182 and fixation targets 191 and 291.

In accordance with a further aspect of the present invention, crossed polarizers 181 and 182 are utilized, one polarizer 181 in the illumination path and polarizer 182 in the observation path of the fundus camera. Polarizer 181 in the illumination path produces substantially linearly polarized light and crossed polarizer 182 in the observation path eliminates light from the illumination path which is reflected by the cornea, or by ocular lens 100. The fundus primarily scatters and, therefore, primarily produces non-polarized light. As a result, presence of the crossed polarizer 182 in the observation path increases the signal reflected from the fundus when compared with light from the illumination path which is reflected by the cornea or by ocular lens 100. This aspect of the present invention is superior to a prior art practice of tilting ocular lens 100 to reduce reflections therefrom from entering the observation path. The superiority of the present invention results from the fact that tilting of ocular lens 100 produces vignetting of the sample beam.

In accordance with a still further aspect of the present invention which is illustrated in FIG. 5, reflection from ocular lens 100 is removed by placing physical stop 161 in beam 185, between lens 160 and light source 150. Physical stop 161 is imaged onto ocular lens 100 to produce a hollow cone of illumination. As a result, ocular lens 100 is not illuminated at the center.

A yet still further aspect of the present invention addresses a problem which is caused by the fact that the field of view of the viewing system of fundus camera 4000 is limited. As a result of this, a patient's eye must be rotated to move a field of interest into the center of the field of view of the fundus camera. This is done, in accordance with the prior art, by shining an external fixation light into the patient's other eye, i.e., the eye which is not being examined. However, in accordance with the present invention, an internal fixation target is used to guide the patient's eye so that the new field of interest becomes centered and can be scanned by the OCT sample beam. The internal fixation target is developed by placing an object such as, for example, needle 191, into the intermediate image of the fundus. To do this, for example, the object is placed in the illumination path shown in FIG. 5A between physical stop 161 and source 150. Then, the patient sees the shadow of the object without blocking the observation path. In an alternative to the use of an object, a visible light source such as, for example, a visible LED is located in the image plane of a video port of the fundus camera. In accordance with the present invention, light 291 source is fixed to plate 293 which is manually movable in the x- and y-directions in a mount located at an image plane conjugate to CCD target 140. In practice, light source 291 is coupled into the camera between tube lens 130 and internal focusing lens 120 by, for example, beamsplitter 297.

In order to provide successful OCDR, image acquisition time must be very short because of saccadic movements of the eye. The image acquisition speed of apparatus described in the art is limited by the maximum speed of a translation stage of a reference mirror and by the amplitude of displacement of the reference mirror. In accordance with OCDR, the amplitude must be in the range of the thickness of the sample, for example, the retina. However, in practice it is necessary to choose a much larger amplitude to overcome the difficulty of focusing onto the fundus with the necessary precision. The translation stage in the art is driven with a sawtooth-like voltage. However, for high frequencies, the response of the mechanical system becomes more or less sinusoidal because high frequency components of the sawtooth function are not transmitted by the damped mechanical system. This is a serious drawback for OCDR because the heterodyne signal is bandpass filtered to eliminate the 1/f noise of the detection system. If the Doppler shift varies in a sinusoidal fashion due to movement of the reference mirror, the duty cycle of the detection system decreases considerably because the signal passes a bandpass filter only in that phase of mirror oscillation where the Doppler shifted signal fits into the bandpass filter.

Figure 6:
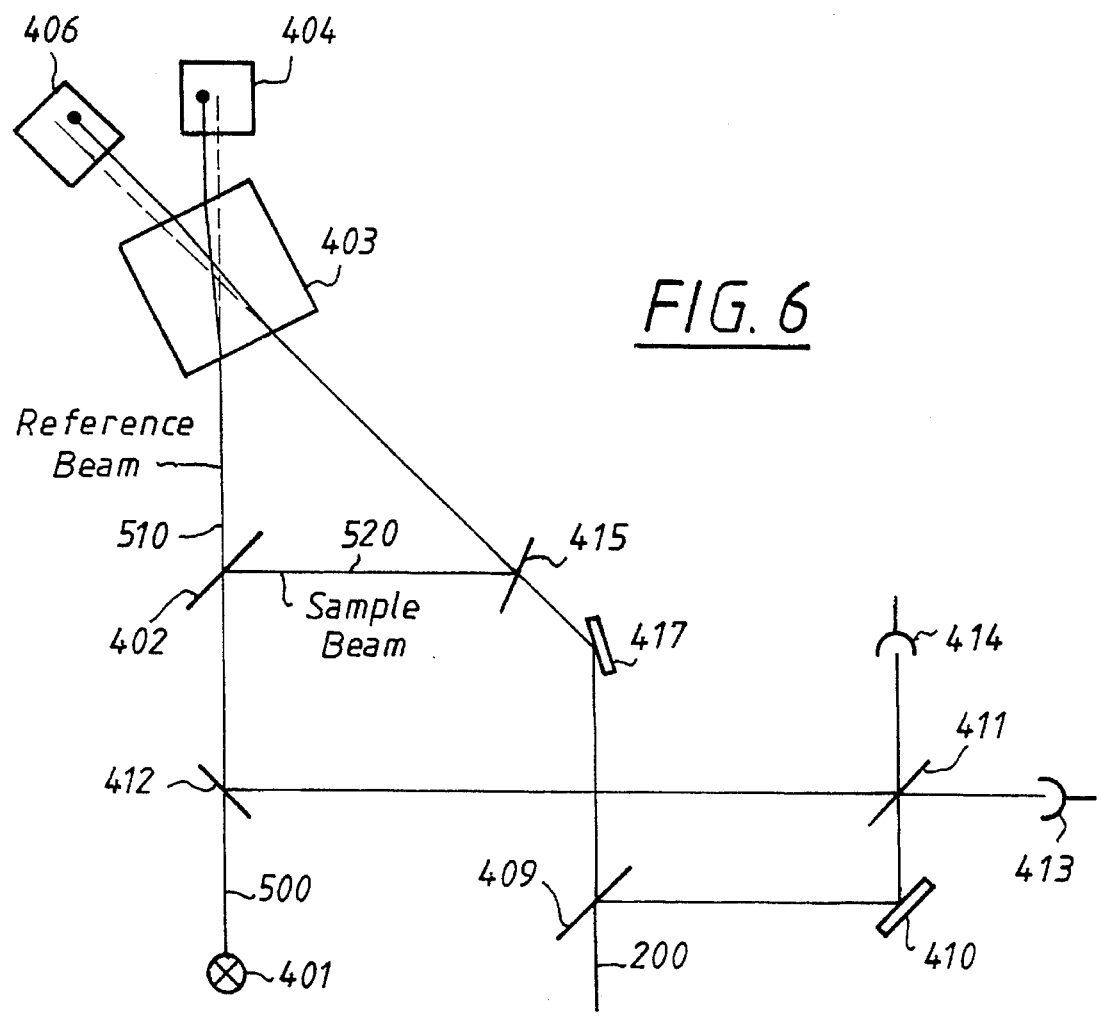
FIG. 6 shows, in pictorial form, a preferred embodiment of OCDR which is utilized in OCT.

FIG. 6 shows, in pictorial form, a preferred embodiment of OCDR which is utilized in OCT. As shown in FIG. 6, beam 500 which is emitted by source 401, for example, a superluminescent diode, is split by beamsplitter 402 into reference beam 510 and sample beam 520. Reference beam 510: (a) passes through rotating glass plate 403; (b) hits retroreflecting prism 404 and is reflected back, with a vertical offset; and (c) passes through glass plate 403 again. Glass plate 403 has four facets of equal length and introduces a periodic change in the optical path in a manner which will be described below. Sample beam 520 is reflected at mirror 415 and passes through glass plate 403 at a 45 degree angle with respect to reference beam 510. The sample beam strikes retroreflecting prism 406 and is reflected back in a deeper plane through glass plate 403 so that it passes underneath mirror 415 and strikes mirror 417. Glass plate 403 introduces a periodic change in the optical path which has the same period as that of reference beam 510, but with an offset of 45 degrees. The resulting path length difference between reference beam 510 and sample beam 520 is linear. Further, since glass plate 403 is symmetric, and the angle between reference beam 510 and sample beam 520 is substantially equal to 45 degrees, one obtains a symmetrical, sawtooth-like path variation and, therefore, a constant Doppler frequency. The Doppler frequency $f=2v/c$, where c is the velocity of light and v is the "pathlength difference velocity" which will be described below. Advantageously, in accordance with the present invention, the fact that glass plate 403 is a symmetrical four facet polygon provides that a sawtooth-like path length variation can be achieved. Further, in accordance with the present invention, the fact that the angle between reference beam 510 and sample beam 520 is substantially equal to 45 degrees provides that the sawtooth is symmetrical.

Figure 8:
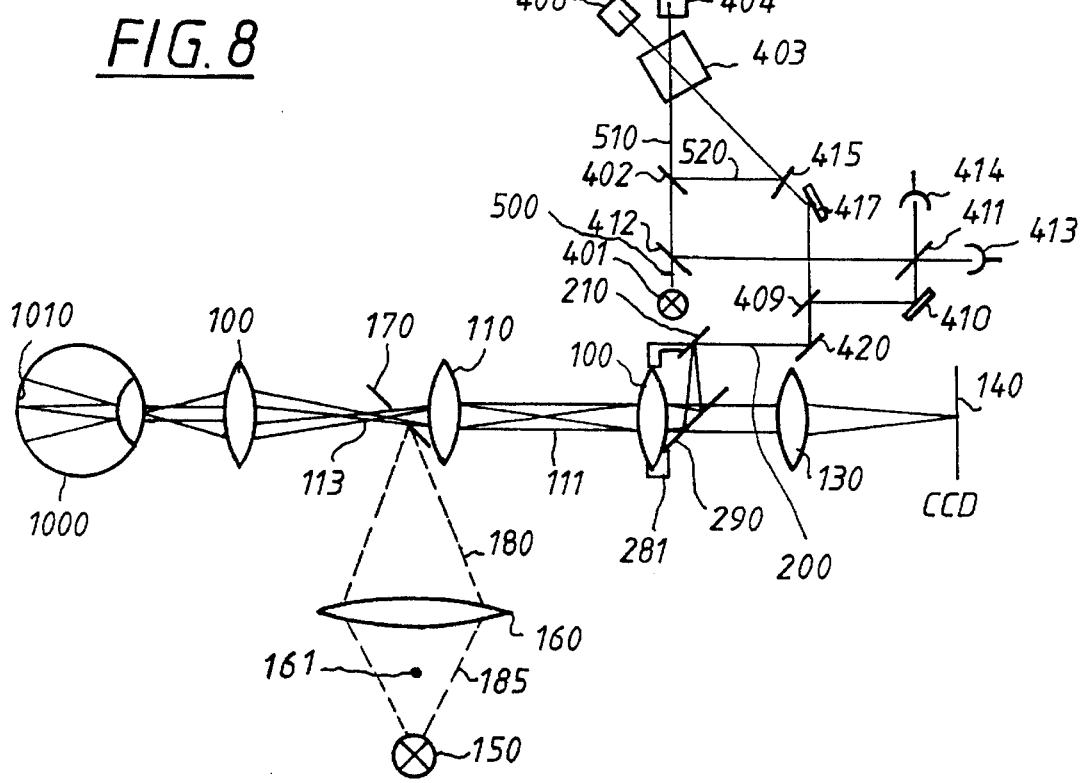
FIG. 8 shows, in pictorial form, an embodiment of the present invention formed from the combination of apparatus shown in FIGS. 5 and 6.

As further shown in FIG. 6, sample beam 520 is deflected by mirror 417 into sample beam 200 which was utilized as described above in conjunction with FIGS. 3 and 5. For example, FIG. 8 shows, in pictorial form, an embodiment of the present invention formed from the combination of apparatus shown in FIGS. 5 and 6. As those skilled in the art readily appreciate, the sample beam may be injected into an optical fiber. Reflections from fundus 1010 are deflected by beamsplitter 409 and mirror 410 to beamsplitter 411. The reflected sample beam is then superimposed with reference beam 510 which is reflected by mirror 412 (mirror 412 is located underneath beam 500 which emerges from source 401). Finally, detectors 413 and 414 measure periodic interference signals as a function of time and with frequencies equal to the Doppler frequency in a manner which has been described in the prior art. The phase difference of the two signals is 180 degrees, which difference is compensated for in a manner which is well known in the art so that the two signals can be added to increase the signal to noise ratio.

Although the apparatus shown in FIG. 6 and described above is utilized in an OCT fundus imaging apparatus, it is within the spirit of the present invention that the apparatus can be utilized in a ranging device for an autofocus system having a high capture range, a distance sensor for measurement of surface topography with micron resolution, and so forth.

Figure 7:
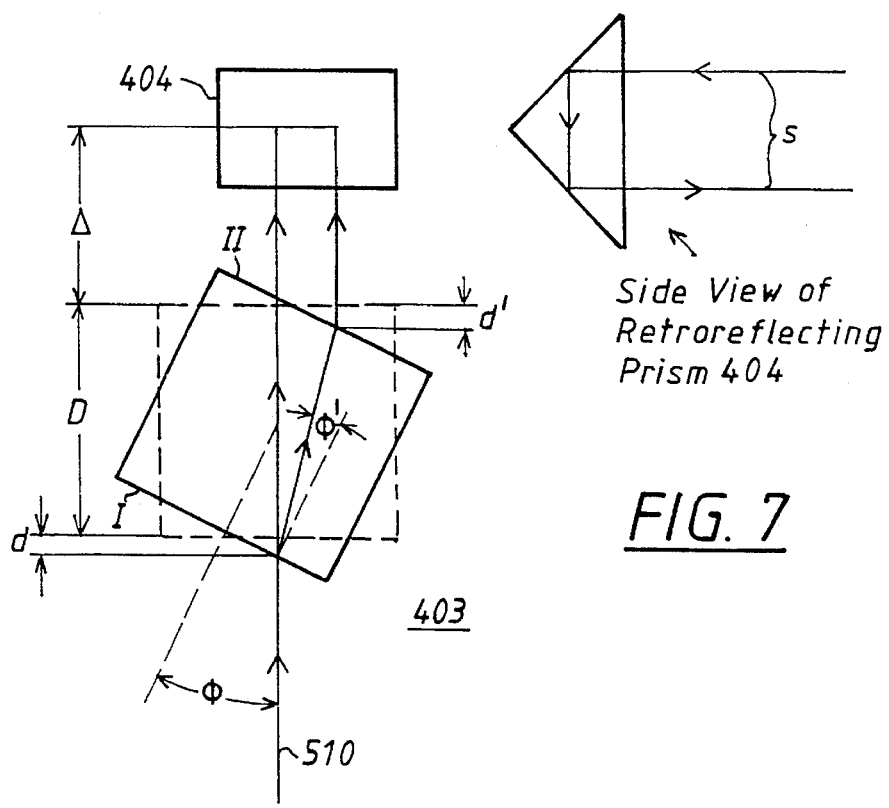
FIG. 7 shows, in pictorial form, glass plate 403 and various views of retroreflecting prism 404.

FIG. 7 shows, in pictorial form, glass plate 403 and various views of retroreflecting prism 404. Glass plate 403 rotates, and the rotation angle $\phi$ is defined to be zero when glass surface I is perpendicular to incoming beam 510. As shown in FIG. 7, incoming beam 510 is refracted at glass surface I with an angle $\phi'$ which is related to the rotational angle $\phi$ of glass plate 403 by Snell's law:

$$\sin \phi' = \sin (\phi)/n$$

where n is the index of refraction of glass plate 403.

Beam 510 passes through glass plate 403 and is refracted again at surface II. For reasons of symmetry, the outgoing beam is parallel to the incoming beam. The outgoing beam hits retroreflecting prism 404 which is disposed perpendicular to the outgoing beam. As a result, the outgoing beam is reflected back towards glass plate 403 in a plane which is deeper than the plane of the incoming beam by an offset s, as shown in a side view of retroreflecting prism 404 in FIG. 7. Hence, the beam passes through glass plate once more, but deeper. The length of this optical path has to be compared with the optical pathlength that beam 510 experiences when it passes through glass plate 403 in a non-tilted position.

The difference of the optical paths of the non-tilted and tilted positions of glass plate 403 are a function of rotation angle $\phi$ which is given by:

$$W(\phi) = D(n-1) - nD/\cos\phi' + D \cos (\phi - \phi')/\cos\phi'$$

where D is the length of a side of glass plate 403 and $\phi' = \arcsin(\sin(\phi)/n)$. The optical pathlength difference is a nonlinear function of $\phi$.

However, sample beam 520 passes through glass plate 403 at a 45 degree angle relative to reference beam 510. The pathlength variation of sample beam 520 due to rotating glass plate 403 is the same as has been set forth above for reference beam 510, but with an offset of $\pi/4$. However, the resulting pathlength variation for reference beam 510 and sample beam 520 is substantially linear and, because of the symmetry of glass plate 403 and the fact that the angle between reference beams 510 and sample beam 520 is substantially equal to 45 degrees, one obtains a symmetrical saw tooth like path variation. The pathlength difference velocity is equal to the product of the rate of change of $W(\phi) - W(\phi - /4)$ with $\phi$ multiplied by the angular velocity of glass plate 403.

In preferred embodiments of the present invention beamsplitters 220 and 290 are dichroic beamsplitters which are known in the art for reflecting wavelengths in the range of the sample beam and for transmitting other wavelengths. However, in alternative embodiments of the present invention, beamsplitters 220 and 290 could be replaced by a minus filter which is known in the art which reflects only wavelengths in the range of the sample beam and transmits other wavelengths.

Those skilled in the art will recognize that the foregoing description has been presented for the sake of illustration and description only. As such, it is not intended to be exhaustive or to limit the invention to the precise form disclosed. For example, modifications and variations are possible in light of the above teaching which are considered to be within the spirit of the present invention. Thus, it is to be understood that the claims appended hereto are intended to cover all such modification and variations which fall within the true scope and spirit of the invention.

What is claimed is:

1. Apparatus for illuminating the fundus of an eye with a beam of radiation output from a beam scanner, the apparatus comprises:

means for transferring radiation from the output beam of radiation, including chief rays of the output beam of radiation which emerge from a point of final deflection of the beam scanner; and means for focusing the transferred radiation so that the output beam of radiation is focused onto the fundus of the eye;

wherein the means for transferring comprises a lens means which is fixed with respect to the beam scanner so that the point of final deflection is located substantially in the back focal plane of the lens means and wherein the lens means is movable.

2. The apparatus of claim 1 further comprises a fundus camera which includes an ocular lens wherein the means for focusing includes the ocular lens and means for directing the transferred radiation to impinge upon the ocular lens.

3. The apparatus of claim 2 wherein the means for directing comprises a beamsplitter disposed to direct output from the lens means to the ocular lens.

4. The apparatus of claim 3 which further comprises a compensation plate disposed in an observation path of the fundus camera to compensate for shifting of an optical axis of the fundus camera caused by the beamsplitter.

5. The apparatus of claim 2 wherein the fundus camera comprises an illumination source and an illumination focusing means for providing an illumination path between the illumination source and the ocular lens, the apparatus further comprises light stop means disposed in the illumination path between the illumination source and the focusing means to provide a hollow cone of illumination radiation which impinges upon the ocular lens.

6. The apparatus of claim 2 wherein the fundus camera comprises an illumination source and an illumination focusing means for providing an illumination path between the illumination source and the ocular lens and wherein the fundus camera further comprises observation focusing means for providing an observation path for receiving reflections from the eye of illumination radiation from the illumination source, the apparatus further comprises linearly polarizing means disposed in the illumination path and linearly polarizing means disposed in the observation path, a direction of its linear polarization being substantially orthogonal to a direction of linear polarization of the polarizing means disposed in the illumination path.

7. The apparatus of claim 2 wherein the fundus camera comprises an illumination source and an illumination focusing means for providing an illumination path between the illumination source and the ocular lens, the apparatus further comprises fixation means disclosed in the illumination path between the illumination source and the illumination focusing means for providing a fixation target in an intermediate image of the fundus which is formed behind the ocular lens in the illumination path.

8. The apparatus of claim 2 wherein the fundus camera comprises a video port disposed in an observation path of the fundus camera, the apparatus further comprises a visible light source and means for transferring output from the visible light source to an image plane of the video port, the visible light source being movable.

9. Apparatus, including a fundus camera, for illuminating the fundus of an eye with a beam of radiation output from a beam scanner, the apparatus comprises:

means for transferring radiation from the output beam of radiation, including chief rays of the output beam of radiation which emerge from a point of final deflection of the beam scanner; and means for focusing the transferred radiation so that the output beam of radiation is focused onto the fundus of the eye;

wherein the means for transferring comprises an internal focusing lens means of the fundus camera wherein the internal focusing lens means is fixed with respect to the beam scanner so that the point of final deflection is located substantially in the back focal plane of the internal focusing lens means and wherein the internal focusing lens means is movable.

10. The apparatus of claim 9 wherein the means for transferring further comprises a beamsplitter disposed to direct the output beam of radiation to impinge upon the internal focusing lens.

11. The apparatus of claim 9 wherein the fundus camera comprises an illumination source and an illumination focusing means for providing an illumination path between the illumination source and an ocular lens of the fundus camera, the apparatus further comprises light stop means disposed in the illumination path between the illumination source and the focusing means to provide a hollow cone of illumination radiation which impinges upon the ocular lens.

12. The apparatus of claim 9 wherein the fundus camera comprises an illumination source and an illumination focusing means for providing an illumination path between the illumination source and an ocular lens of the fundus camera and wherein the fundus camera further comprises observation focusing means for providing an observation path for receiving reflections from the eye of illumination radiation from the illumination source, the apparatus further comprises linearly polarizing means disposed in the illumination path and linearly polarizing means disposed in the observation path, a direction of its linear polarization being substantially orthogonal to a direction of linear polarization of the polarizing means disposed in the illumination path.

13. The apparatus of claim 9 wherein the fundus camera comprises an illumination source and an illumination focusing means for providing an illumination path between the illumination source and an ocular lens of the fundus camera, the apparatus further comprises fixation means disposed in the illumination path between the illumination source and the illumination focusing means for providing a fixation target in an intermediate image of the fundus which is formed behind the ocular lens in the illumination path.

14. The apparatus of claim 9 wherein the fundus camera comprises a video port disposed in an observation path of the fundus camera, the apparatus further comprises a visible light source and means for transferring output from the visible light source to an image plane of the video port, the visible light source being movable.

15. Apparatus for use in optical coherence tomography which includes a Doppler shifter, the Doppler shifter comprising:

means for splitting a beam into a reference beam and a sample beam;

a rotatable, refractive, light transmissive block, the block having four substantially equal length sides formed into a square;

means for rotating the block;

means for directing the reference beam to impinge on the block in a reference direction and means for directing the sample beam to impinge upon the block in a sample direction, the reference direction and the sample direction being disposed substantially at a 45 degree angle with respect to each other; and a first and a second reflecting means disposed behind the block to reflect the reference beam and the sample beam emerging therethrough back through the block.

16. Method for illuminating the fundus of an eye with a beam of radiation output from a beam scanner, the method comprises the steps of:

transferring radiation from the output beam of radiation, including chief rays of the output beam of radiation which emerge from a point of final deflection of the beam scanner; and focusing the transferred radiation so that the output beam of radiation is focused onto the fundus of the eye;

wherein the step of transferring comprises transferring with a movable lens which is fixed with respect to the beam scanner so that the point of final deflection is located substantially in the back focal plane of the lens.

17. Method for illuminating the fundus of an eye with a beam of radiation output from a beam scanner, the method comprises the steps of:

transferring radiation from the output beam of radiation, including chief rays of the beam of radiation which emerge from a point of final deflection of the beam scanner; and focusing the transferred radiation so that the output beam of radiation is focused onto the fundus of the eye;

wherein the step of transferring comprises transferring with a beamsplitter which is fixed with respect to the beam scanner and a movable focusing lens so that the point of final deflection is located substantially in the back focal plane of the focusing lens.

* * * * *

(12) EX PARTE REEXAMINATION CERTIFICATE (9167th)

United States Patent
Hellmuth et al.

(10) Number: US 5,537,162 C1
(45) Certificate Issued: Aug. 7, 2012

(54) METHOD AND APPARATUS FOR OPTICAL COHERENCE TOMOGRAPHIC FUNDUS IMAGING WITHOUT VIGNETTING

(75) Inventors: Thomas Hellmuth, Danville, CA (US); Jay Wei, Fremont, CA (US)

(73) Assignee: Carl Zeiss Meditec, Inc., Dublin, CA (US)

Reexamination Request:
No. 90/012,007, Nov. 14, 2011

Reexamination Certificate for:
Patent No.: 5,537,162
Issued: Jul. 16, 1996
Appl. No.: 08/169,705
Filed: Dec. 17, 1993

(51) Int. Cl.
*A61B 3/14* (2006.01)
*A61B 3/10* (2006.01)

(52) U.S. Cl. .................. 351/206; 351/211; 351/221
(58) Field of Classification Search ................. None
See application file for complete search history.

(56) References Cited

To view the complete listing of prior art documents cited during the proceeding for Reexamination Control Number 90/012,007, please refer to the USPTO's public Patent Application Information Retrieval (PAIR) system under the Display References tab.

*Primary Examiner* — Robert Nasser

(57) ABSTRACT

Apparatus for illuminating the fundus of an eye with a scanned sample beam of radiation, the scanned sample beam emerging from a beam scanner which is exposed to a sample beam, which apparatus is for use in optical coherence tomography. An embodiment of the apparatus includes: (a) scanner lens and a beamsplitter for transferring radiation from the scanned sample beam, including chief rays of the sample beam which emerge from a point of final deflection of the beam scanner, and (b) a lens for focusing the transferred radiation so that the scanned sample beam is focused onto the fundus by the eye. In accordance with the invention the scanner lens is fixed with respect to the beam scanner so that the point of final deflection is located substantially in the back focal plane of the scanner lens and the scanner lens is movable.

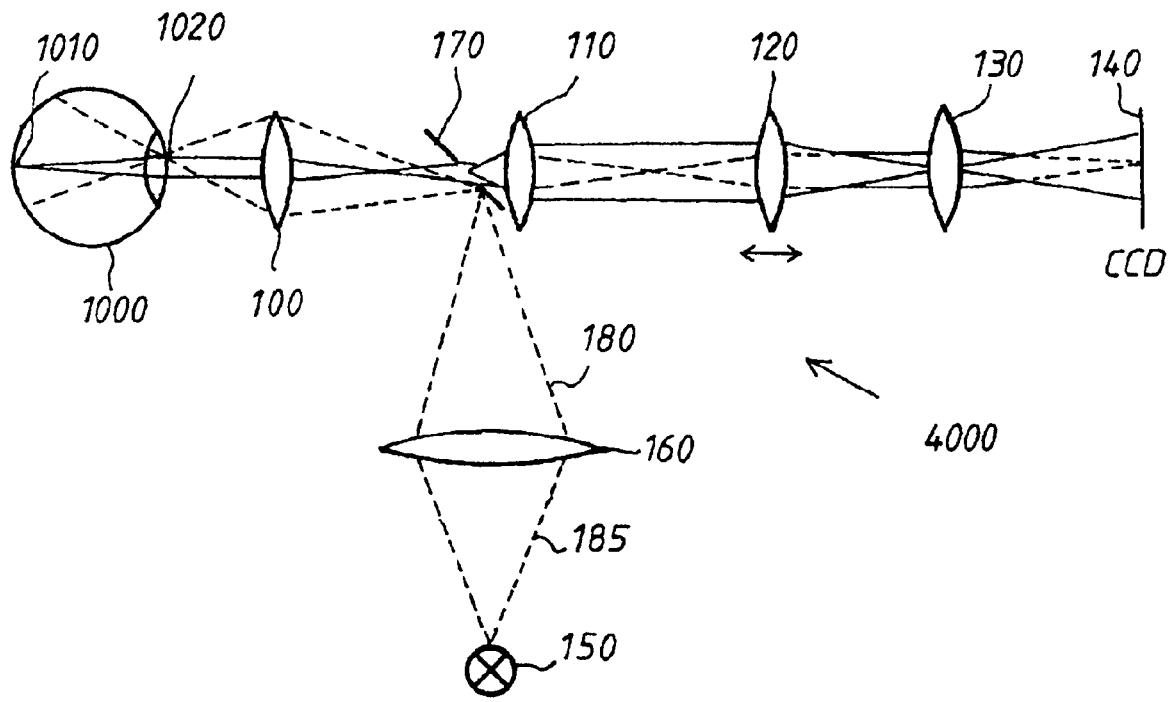

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-3, 5, 7, 9-11, 13, 16 and 17 are cancelled.

Claims 4, 6, 8, 12, 14 and 15 were not reexamined.

\* \* \* \* \*